(12) United States Patent
Choudary et al.

(10) Patent No.: US 6,703,532 B2
(45) Date of Patent: Mar. 9, 2004

(54) PROCESS FOR THE NITRATION OF XYLENE ISOMERS USING ZEOLITE BETA CATALYST

(75) Inventors: Boyapati Manoranjan Choudary, Andhra Pradesh (IN); Mannepalli Lakshmi Kantam, Andhra Pradesh (IN); Nadakuditi Sailendra Kumar, Andhra Pradesh (IN); Kompella Vishweshwara Ram Prasad, Andhra Pradesh (IN); Kondapuram Vijaya Raghavan, Andhra Pradesh (IN)

(73) Assignee: Council of Scientific and Industrial Research, New delhi (IN)

( * ) Notice: Subject to any disclaimer, the term of this patent is extended or adjusted under 35 U.S.C. 154(b) by 99 days.

(21) Appl. No.: 10/032,380

(22) Filed: Dec. 21, 2001

(65) Prior Publication Data

US 2003/0166980 A1 Sep. 4, 2003

(51) Int. Cl.$^7$ .............................................. C07C 205/00
(52) U.S. Cl. ...................................... 568/940; 568/939
(58) Field of Search ................................. 568/939, 940

(56) References Cited

U.S. PATENT DOCUMENTS 3,929,916 A * 12/1975 Levy et al. ................. 568/940

OTHER PUBLICATIONS

NaGi et al, Production of mixture of nitro–ortho–xyleneby nitration of ortho–xylene with concentrated nitric acid, Abstract of SU 1710546 A1, Jun. 23, 1989.*

Testova et al, Gas phase nitration of aromatic hydrocarbons on zeolite catalyst, Chemistry, Ecology, Health, proceedings of International on zeolite catalysis, Jan. 6–12, (1995) pp. 137–154.*

* cited by examiner

Primary Examiner—J. Parsa
(74) Attorney, Agent, or Firm—Ladas & Parry

(57) ABSTRACT

This invention relates to a process for the nitration of xylene isomers by using zeolite-beta as a catalyst. This invention particularly relates to a process for the nitration of xylenes using solid acid catalyst, thus totally eliminating the disposal of spent acid and salts. Herein we describe the nitration of disubstituted benzenes, all the isomers of xylene, by employing nitric acid and beta zeolite catalyst dispensing the use of acetic anhydride. The reactions were performed at temperatures ranging from room temperature to reflux temperature of the solvent

17 Claims, No Drawings

PROCESS FOR THE NITRATION OF XYLENE ISOMERS USING ZEOLITE BETA CATALYST

This invention relates to a process for the nitration of xylene isomers by using zeolite-beta as a catalyst. This invention particularly relates to a process for the nitration of xylenes using solid acid catalyst, thus totally eliminating the disposal of spent acid and salts.

Nitration has been an active area of industrial chemistry for over a century. Nitration process is used for the production of many large-volume chemicals such as nitroaromatics. The production of mixtures of aromatic nitro compounds in different isomeric proportions from those usually obtained in direct nitrations and the nitration of compounds that are usually unreactive would be of synthetic importance. These nitroaromatics are vital intermediates for dyes, pharmaceuticals, pesticides, perfumes and pesticides. In nitrations, normally 1,2-disubstituted benzenes often pose more problems of selectivity than do monosubstituted benzenes.

Nitration of xylenes is performed by the classical method employing the $H_2SO_4$—$HNO_3$ system. The selectivities in the nitration of xylenes using mixed $H_2SO_4$-$HNO_3$ are: 3nitro-o-xylene and 4nitro-o-xylene from o-xylene are 55% and 45% respectively while that of 2-nitro-m-xylene and 4-nitro-m-xylene from m-xylene are 14% and 86% respectively. The mixed acid system not only displays low isomeric selectivity in the nitration of mono and disubstituted aromatic nitro compounds, but also it is corrosive and invariably used in excess that often leads to over-nitrated products or oxidized by-products. Another major disadvantage of this process is the disposal of the spent acid.

Recent attention has been focused on the development of environmentally friendly solid acid catalysts such as zeolites, sulfated zirconia and Nafion especially to perform Friedel-Crafts nitration reactions in an effort to replace environmentally hazardous chemicals.

Reference may be made to J. Org. Chem., 1961, 26, 2536 wherein the 4-nitro-o-xylene was prepared by the nitration of o-xylene which is carried out with uranium nitrate-nitrogen tetroxide water complex in acetic anhydride. The drawbacks in the above process are the use of expensive and hazardous metal complexes, large amount of acetic anhydride which forms insitu explosive acylnitrate and the reaction is a highly exothermic reaction.

Reference may be made to J. Am. Chem. Soc., 1962, 84, 3684 wherein the nitration of the isomers of xylene was carried out with nitronium salts in tetramethylene sulfone and in nitromethane solution at 20° C. The isomeric distribution of nitrocompounds of o- and m-xylenes with tetramethylene sulfone and nitromethane were 79.7%, 68.6% (3-nitro-o-xylene); 20.3%, 31.4% (4-nitro-o-xylene); 17.8%, 14.6% (2-nitro-m-xylene); 4nitro-m-xylene: 82.2%, 85.44. The drawback in the above process is the use of high dilutions, use of excess nitrating reagents and it is a homogeneous process.

Reference may be made to J. Org. Chem., 1973, 38, 2271 wherein the nitration of o-xylene was induced by the aroyl nitrates prepared from the corresponding aroyl chloride and silver nitrate. The demerits of this process are that the reagents used are uneconomical and expensive metallic salts and also the occurrence of benzoylation in addition to nitration.

Reference may be made to J. Am. Chem. Soc., 1974, 96, 2892 wherein the nitration of xylenes was catalysed by $BF_3$. The isomer distribution of the nitro products are: 4-nitro-o-xylene 34.7%; 3-nitro-o-xylene 65.3% in nitration of o-xylene, 2-nitro-m-xylene 16.9%; 4-nitro-m-xylene 83.1% in nitration of m-xylene. The disadvantages of this process was that it is a homogeneous and the yields are relatively low.

Reference may be made to J. Chem. Soc., Perkin Trans. 1, 1974, 1751 wherein the nitration of o- and m-xylene was performed by the nitrato-complexes of zirconium (IV) and iron (III) at room temperature. The selectivities in this process are: 4-nitro-o-xylene (65%) and 3-nitro-o-xylene (35%) in nitration of o-xylene; 2-nitro-m-xylene 10% and 4-nitro-m-xylene 90% in nitration of m-xylene with $Zr(NO_3)_4$ and with $Fe(NO_3)_4NO$ respectively. The demerit of this process was the expensive of nitrating agents.

Reference may be made to J. Chem. Soc., Perkin Trans. 1, 1978, 1076 wherein the nitration of o-xylene was performed with sodium nitrite or nitrate in triflouroacetic acid at room temperature for 8 h with constant stirring. The selectivity of 4-nitro-o-xylene in this process is 47% and 39% with $NaNO_2$ and $NaNO_3$ respectively. The demerits of this process is that it is a hazardous and explosive, non-economical and low selectivity towards 4-nitro-o-xylene.

Reference may be made J. Org. Chem., 1978, 38, 4243 wherein the nitration of m-xylene was performed with anhydrous nitric acid and trifluoromethanesulfonic acid using dichloromethane as a solvent. The demerit of this process was that there is no formation of any mononitro isomer of m-xylene (only dinitro derivatives were formed).

Reference may be made to J. Org. Chem., 1978, 43, 4628 wherein the nitration was performed with n-butyl nitrate, acetone cyanohydrin nitrate catalyzed by a perfluorinated resin sulfonic acid (Nafion-H) catalyst. The nitrations were also performed with nitric acid and dinitrogen tetroxide over Nafion-H catalyst. The conversion is 98%, 98% and 95% for o-, m- and p-xylene respectively. The demerits of these processes are the longer reaction times, use of fuming nitric acid and tedious work-up procedure for the reaction with dinitrogen tetroxide and also use of expensive nitrating agents. Further the Nafion-H resin is expensive and degraded for each cycle and eventually the catalyst has short life.

Reference may be made to J. Org. Chem., 1981, 46, 2706 wherein the nitration was catalyzed by boron triflouride etherate with N-nitropyrazole using dichloromethane as the solvent. The conversion is 96% for p-xylene. The demerit of this process is the use of excess aromatic compound and a homogeneous process.

Reference may be made to J. Org. Chem., 1981, 46, 3533 wherein the nitration was catalyzed with boron triflouride and silver nitrate in acetonitrile solution. The selectivity of the nitro isomers were: 4-nitro-o-xylene 37%, 3-nitro-o-xylene 63% in nitration of o-xylene; 2-nitro-m-xylene— 13% and 5-nitro-m-xylene—87% in nitration of m-xylene. The demerits of this process are the longer reaction times, difficult reaction conditions and work-up procedures.

Reference may be made to J. Chem. Soc., Perkin Trans. 1, 1993, 1591 wherein the nitration of o-xylene is performed under continuous feeding of ozone in the presence of excess of nitrogen dioxide in dichloromethane as a solvent at 0° C. The selectivities of the nitro isomers are: 4-nitro-o-xylene— 46%, 3-nitro-o-xylene—34% in nitration of o-xylene; 2-nitro-m-xylene—9% and 4-nitro-m-xylene—78% in nitration of m-xylene. The demerit of this process is the necessity for continuous feeding of expensive ozone, which is ecounfriendly.

Reference may be made to J. Org. Chem., 1998, 63, 8448 wherein the nitration of o-xylene was performed under mild conditions using beta zeolite as a catalyst and a stoichiometric quantity of nitric acid and acetic anhydride. The conversion was 99% with low selectivities. The demerits of this process are the formation of 3,4-dimethyl-1-acetoxybenzene in 23% yield along with the other isomers and the use of acetic anhydride, which forms an explosive mixture with nitric acid.

In order to overcome the drawbacks in the use of mixed acid system, we earlier developed a process for the nitration of monosubstituted aromatic hydrocarbons using aluminium silicates as catalysts and nitric acid as nitrating agent. We duly filed patents in US, Europe and Japan and already granted U.S. Pat. No. 6,034,287, in 2000 and European Patent no. 1004570 A1 and Japanese Patent no. 95734 A2. Herein we describe the nitration of disubstituted benzenes, all the isomers of xylene, by employing nitric acid and beta zeolite catalyst dispensing the use of acetic anhydride. The reactions were performed at temperatures ranging from room temperature to reflux temperature of the solvent (DCE). Reactions were performed by taking o-xylene and $HNO_3$ in the molar ratio ranging from 0.80 to 1.50. The selectivity of 4-nitro-o-xylene prepared from o-xylene is 68% and that of 4nitro-m-xylene from m-xylene is 87%. The selectivity of 2-nitro-p-xylene from p-xylene is 100% based on p-xylene consumed when the nitration is performed using xylene and $HNO_3$ in the molar ratio of 1:1.2. Azeotropic removal of water formed in the reaction and that present in the nitric acid makes the solid acid catalyst reusable.

The main objective of the present invention is to provide a process for the nitration of isomers of xylene with high selectivity towards 4-nitro o and m-xylenes using zeolite catalyst in batch mode Another objective of the present invention is to provide an improved process for the nitration of xylene isomers with high selectivity towards 4-nitro o- and m-xylenes using modified clay catalysts.

Yet another objective of the present invention is the separation of the isomers using standard vacuum distillation and removing the excess of nitric acid by conventional method.

Yet another objective of the present invention is the azeotropic removal of the water formed during the reaction and that present in the nitric acid and thus permitting the reusability of the solid acid catalyst.

SUMMARY OF THE INVENTION

Accordingly, the present invention provides a process an improved process for the nitration of isomers of xylene with high selectivity towards 4-nitro o and m-xylenes using a zeolite catalyst in batch mode which comprises nitrating the substrate with nitric acid in a molar ratio of xylene to nitric acid in the range of 1:0.80 to 1:1.5 in the presence of a zeolite-β catalyst at a reflux temperature of solvent for about 4 h and recovering the resulting nitro compound by conventional methods.

In an embodiment of the present invention the nitric acid used is added in a controlled manner during the period specified.

In yet another embodiment the nitric acid used is about 70% nitric acid.

In yet another embodiment the ratio of xyline to nitric acid used is preferably in the range of 1:1.0 to 1:1.25.

In yet another embodiment the solvent used for the reaction is selected from the group consisting of dichloroethane, dichloromethane, carbon tetrachloride and xylene itself.

In still another embodiment the reaction is effected at a temperature preferably in the range of 90 to 120° C. for about 4 h.

The following examples are given by way of illustration of the present invention and therefore should not be construed to limit the scope of the present invention.

EXAMPLE 1

50 mmol of o-xylene and 500 mg of catalyst are taken in a 100 ml two-necked round bottomed flask along with 10 ml of dichloroethane and heated to reflux temperature. 4.23 ml of $HNO_3$ (70%) is added continuously over a period of 4 h. The water formed in the reaction is separated by a Dean-Stark apparatus. On completion of the reaction, the reaction mixture is filtered. It is subjected to base wash to remove the excess acid. The isomers formed are separated by vacuum distillation. Varying the rate of addition of nitric acid, a number of nitration of o-xylene reactions were conducted and summarized in the table 1. The optimum rate of addition of nitric is found to be 1 ml/hour.

TABLE I

Nitration of O-xylene with 70% $HNO_3$[1]

| S.No | O-Xylene (mmols) | $HNO_3$ (mmols) | Solvent used | Rate of addn. (ml/hr.) | Selectivity (%) | | |
|---|---|---|---|---|---|---|---|
| | | | | | 3- | 4- | others |
| 1 | 68[a] | 85 | DCE | 24 | 45.0 | 47.0 | 8.0 |
| 2 | 68[a] | 85 | DCE | 12 | 28.0 | 50.0 | 22.0 |
| 3 | 68[a] | 85 | DCE | 12 | 42.0 | 49.0 | 9.0 |
| 4 | 68[a] | 85 | DCE | 12 | 25.0 | 52.0 | 23.0 |
| 5 | 68[a] | 85 | DCE | 12 | 37.0 | 50.0 | 13.0 |
| 6 | 68[a] | 85 | DCE | 6 | 41.0 | 50.0 | 9.0 |
| 7 | 125[b] | 68 | DCE | 3.5 | 34.0 | 52.0 | 14.0 |
| 8 | 50[c] | 60 | DCE | 3.0 | 41.0 | 51.0 | 8.0 |
| 9 | 50[c] | 60 | DCE | 1.5 | 35.0 | 49.0 | 15.0 |
| 10 | 50[c] | 60 | DCE | 1.2 | 38.0 | 45.0 | 13.0 |
| 11 | 50[c] | 60 | DCE | 1.0 | 32.0 | 68.0 | 1.94 |
| 12 | 50[c] | 60 | DCE | 1.5 | 27.0 | 64.0 | 9.0 |

[a]molar ratio of o-xylene to 70% $HNO_3$ is 1:1.25;
[b]molar ratio of o-xylene to 70% $HNO_3$ is 1:1.2
[c]excess of starting material is taken
[1]all the reactions were performed at reflux temperature.
Conversion is at a maximum of 40%

EXAMPLE 2

50 mmol of m-xylene and 500 mg of catalyst are taken in a 100 ml two-necked round bottomed flask along with 10 ml of dichloroethane and heated to reflux temperature. 4.23 ml of $HNO_3$ (70%) is added continuously over a period of 4 h. The water formed in the reaction is separated by a Dean-Stark apparatus. On completion of the reaction, the reaction mixture is filtered. It is subjected to base wash to remove the excess acid. The isomers formed are separated by vacuum distillation.

EXAMPLE 3

50 mmol of p-xylene and 500 mg of catalyst are taken in a 100 ml two-necked round bottomed flask along with 10 ml of dichloroethane and heated to reflux temperature. 4.23 ml of $HNO_3$ (70%) is added continuously over a period of 4 h. The water formed in the reaction is separated by a Dean-Stark apparatus. On completion of the reaction, the reaction mixture is filtered. It is subjected to base wash to remove the excess acid. The isomers formed are separated by vacuum distillation.

The Main Advantages of the Present Invention are

1. The present process is very simple.
2. The catalyst is cheap, non-corrosive and heterogeneous in nature.
3. Lesser quantity of nitric acid is employed.
4. The process is economical.
5. The process is accomplished in a short time.
6. The amount of effluents formed in this process is minimized.

We claim:

1. A process for the nitration of isomers of xylene with high selectivity towards 4-nitro o and m-xylenes using a zeolite catalysy in batch mode which comprises nitrating the substrate with nitric acid in a molar ratio of xylene to nitric acid in the range of 1:080 to 1:1.5 in the presence of a zeolite-β catalyst at a reflux temperature of solvent and recovering the resulting nitro compounds.

2. A process as claimed in claim 1, wherein the nitric acid used is added in a controlled manner during the specified period.

3. A process as claimed in claim 1, wherein the nitric acid used is of about 70% nitric acid.

4. A process as claimed in claim 1, wherein the molar ratio of xylene to nitric acid used is in the range 1:1.0 to 1:1.25.

5. A process as claimed in claim 1, wherein the solvent used for the reaction is selected from the group consisting of dichloroethane, dichloromethane, carbon tetrachloride and xylene itself.

6. A process as claimed in claim 1, wherein the reaction is effected at a temperature in the range of 90 to 120° C. for about 4 h.

7. A process as claimed in claim 2, wherein the nitric acid used is of about 70% nitric acid.

8. A process as claimed in claim 2, wherein the molar ratio of xylene to nitric acid used is in the range 1:1.0 to 1:1.25.

9. A process as claimed in claim 3, wherein the molar ratio of xylene to nitric acid used is in the range 1:1.0 to 1:1.25.

10. A process as claimed in claim 2, wherein the solvent used for the reaction is selected from the group consisting of dichloroethane, dichloromethane, carbon tetrachloride and xylene itself.

11. A process as claimed in claim 3, wherein the solvent used for the reaction is selected from the group consisting of dichloroethane, dichloromethane, carbon tetrachloride and xylene itself.

12. A process as claimed in claim 4, wherein the solvent used for the reaction is selected from the group consisting of dichloroethane, dichloromethane, carbon tetrachloride and xylene itself.

13. A process as claimed in claim 2, wherein the reaction is effected at a temperature in the range of 90 to 120° C. for about 4 h.

14. A process as claimed in claim 3, wherein the reaction is effected at a temperature in the range of 90 to 120° C. for about 4 h.

15. A process as claimed in claim 4, wherein the reaction is effected at a temperature in the range of 90 to 120° C. for about 4 h.

16. A process as claimed in claim 5, wherein the reaction is effected at a temperature in the range of 90 to 120° C. for about 4 h.

17. A process as claimed in claim 1 wherein the reaction at reflux temperature is carried out for about 4 h.

* * * * *